US00PP19997P2

(12) United States Plant Patent
Danziger

(10) Patent No.: US PP19,997 P2
(45) Date of Patent: May 12, 2009

(54) ***TORENIA* PLANT NAMED 'DANCAT153'**

(50) Latin Name: ***Torenia* sp.**
Varietal Denomination: DANCAT153

(75) Inventor: Gabriel Danziger, Moshav Nir-Zvi (IL)

(73) Assignee: Danziger "Dan" Flower Farm, Post Beit Dagan (IL)

( * ) Notice: Subject to any disclaimer, the term of this patent is extended or adjusted under 35 U.S.C. 154(b) by 0 days.

(21) Appl. No.: 12/003,822

(22) Filed: Jan. 2, 2008

(51) Int. Cl.
*A01H 5/00* (2006.01)

(52) U.S. Cl. ..... Plt./487

(58) Field of Classification Search ..... Plt./487
See application file for complete search history.

*Primary Examiner*—June Hwu
(74) *Attorney, Agent, or Firm*—Foley & Lardner LLP

(57) ABSTRACT

A new and distinct *Torenia* plant named 'DANCAT153' particularly characterized by plenty of delicate, funnel form, cup-shaped, white flowers with a yellow blotch on lower petal; cascading bush, which maintains a compact, rounded plant habit; vigorous growth habit; densely branched plant, gracefully cascading from hanging baskets; early flowering response and stays in full bloom in moderate climate; suitable as an annual for hanging pots outdoors under partial shade; and good weather tolerance with a preferred temperature range of 15° C. to 25° C.

2 Drawing Sheets

Latin name of the genus and species of the plant claimed: *Torenia* sp.
Variety denomination: 'DANCAT153'.

BACKGROUND OF THE INVENTION

The present invention relates to a new and distinct cultivar of *Torenia* plant, botanically known as *Torenia* sp. of the *Scrophulariaceae* family, and hereinafter referred to by the cultivar name 'DANCAT153'.

The new *Torenia* cultivar is a product of a planned breeding program conducted by the inventor, Gabriel Danziger, in Moshav Mishmar Hashiva, Israel. The objective of the breeding program was to develop a new *Torenia* cultivar with abundant white flowers.

The new *Torenia* cultivar originated from an induced mutation by radiation of the Torenia 'DANCATBLUE' (patented, U.S. Plant Pat. No. 16,949 and Canadian PBR Grant No. 2527). The new Torenia cultivar was discovered and selected by the inventor, Gabriel Danziger, as a single flowering plant within the progeny of the stated mutation in a controlled greenhouse environment in February of 2005 in Moshav Mishmar Hashiva, Israel.

Asexual reproduction of the new *Torenia* cultivar by vegetative cuttings was first performed in March of 2005 in Moshav Mishmar Hashiva, Israel, and has demonstrated that the combination of characteristics as herein disclosed for the new cultivar are firmly fixed and retained through successive generations of asexual reproduction. The new cultivar reproduces true to type.

BRIEF DESCRIPTION OF THE INVENTION

The following traits have been repeatedly observed and are determined to be basic characteristics of 'DANCAT153' which in combination distinguish this *Torenia* as a new and distinct cultivar:

1. Plenty of delicate, funnel form, cup-shaped, white flowers with a yellow blotch on lower petal;
2. Cascading bush, which maintains a compact, rounded plant habit;
3. Vigorous growth habit;
4. Densely branched plant, gracefully cascading from hanging baskets;
5. Early flowering response and stays in full bloom in moderate climate;
6. Suitable as an annual for hanging pots outdoors under partial shade; and
7. Good weather tolerance with a preferred temperature range of 15° C. to 25° C.

Plants of the new *Torenia* 'DANCAT153' differ from plants of the parental cultivar, *Torenia* 'DANCATBLUE' (patented) in the characteristics described in Table 1.

TABLE 1

| Characteristic | New Cultivar 'DANCAT153' | Parental Cultivar 'DANCATBLUE' (patented) |
|---|---|---|
| Mature flower color | White petals with a yellow blotch on lower petal | Pale violet-blue petals with violet-blue blotches on the side petals, with a centered yellow-green blotch near the base |
| Flower size | Depth: About 3 cm<br>Width: About 3.5 cm | Depth: About 3 cm<br>Width: About 2.8 cm |
| Plant form | Bush cascading | Bush cascading |
| Flowering Response Time | 7 weeks from planting | 8 weeks from planting |

Of the many commercial cultivars known to the present inventor, the most similar in comparison to the new *Torenia* 'DANCAT153' is the *Torenia* 'DANTOHONEYMON' (patented, U.S. Plant Pat. No. 17,187), described in Table 2:

TABLE 2

| Characteristic | New Cultivar 'DANCAT153' | Comparison Cultivar 'DANTOHONEYMON' (patented) |
|---|---|---|
| Mature flower color | White petals with a yellow blotch on lower petal | Pale red-purple and pink petals, with a yellow blotch on lower petal |
| Flower size | Depth: About 3 cm<br>Width: About 3.5 cm | Depth: About 3 cm<br>Width: About 3 cm |
| Plant form | Bush cascading | Bush cascading |
| Flowering response time | 7 weeks from planting | 9 weeks from planting |

BRIEF DESCRIPTION OF THE PHOTOGRAPHS

The accompanying photographs illustrate the overall appearance of the new *Torenia* 'DANCAT153' showing the colors as true as is reasonably possible with colored reproductions of this type. Colors in the photographs may differ slightly from the color values cited in the detailed botanical description, which accurately describe the color of 'DANCAT153'.

DETAILED BOTANICAL DESCRIPTION

Figure 1:
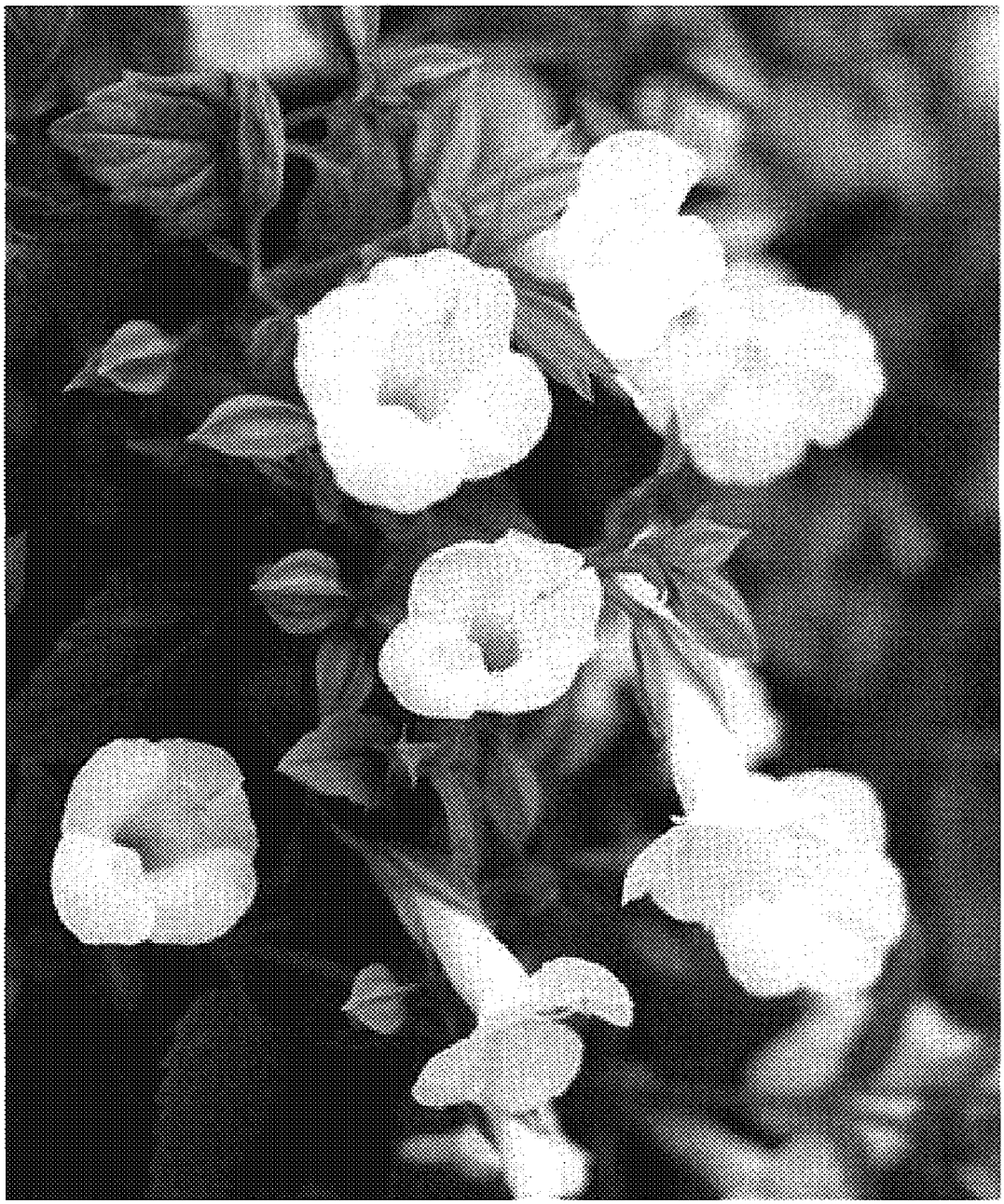
FIG. 1 shows a close-up of the typical flowers, buds and leaves of 'DANCAT153' at 3 months of age.
Figure 2:
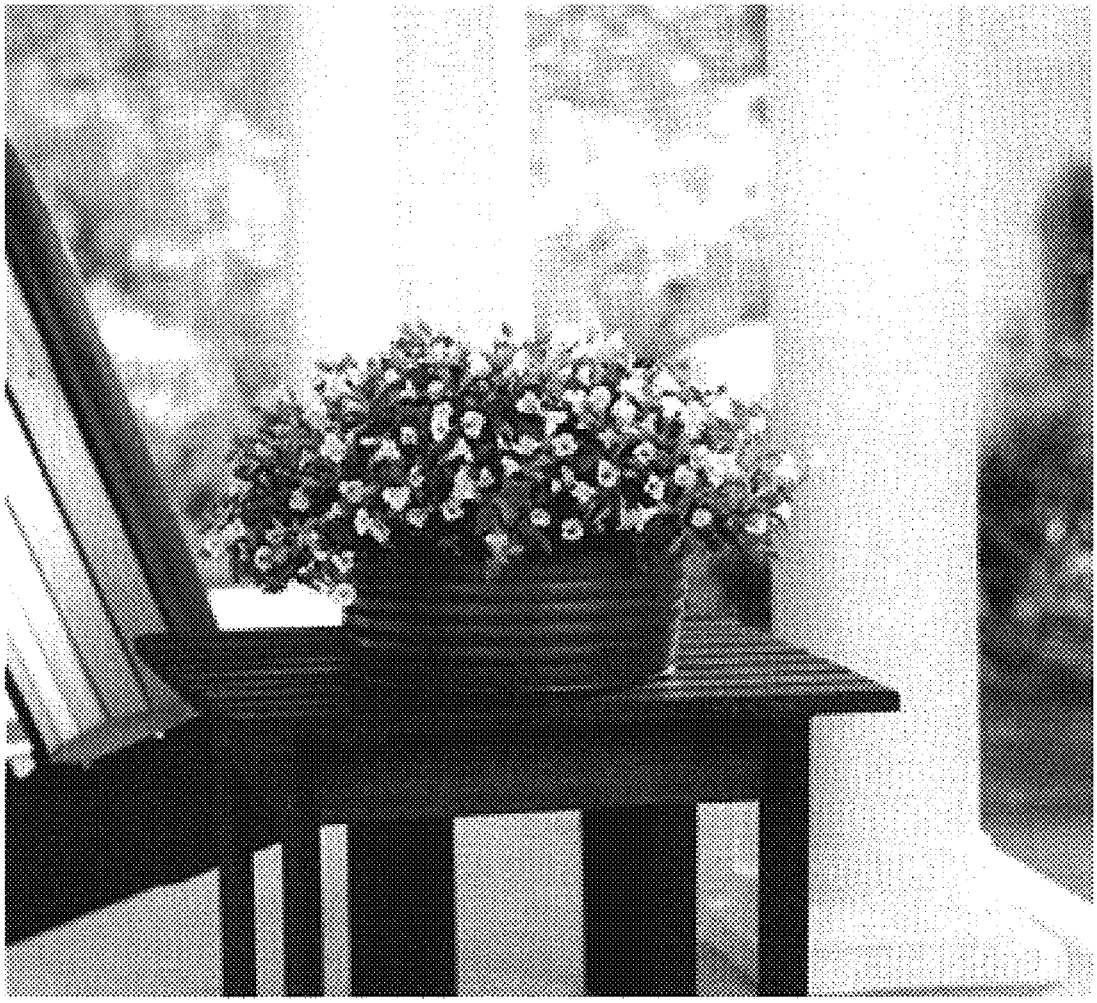
FIG. 2 shows a side perspective view of a typical flowering plant of 'DANCAT153' in a 13 cm planter at 3 months of age.

The new *Torenia* 'DANCAT153' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'DANCAT153' as grown in a greenhouse in Moshav Mishmar Hashiva, Israel, under conditions which closely approximate those generally used in commercial practice. Optimal growth conditions include that plants of 'DANCAT153' are grown outdoors in a moderate climate and indoors during the winter season. Irrigation and fertilization are recommended on a regular basis. Plants of 'DANCAT153' are usually grown in full sunlight, but partial shade is required in mid summer. Plants of 'DANCAT153' are fully grown in 3 months from planting a cutting in the summer season and bloom all year-round in a moderate climate. The 'DANCAT153' plants described herein were grown indoors in 13 cm pots in a glass greenhouse in Moshav Mishmar Hashiva, Israel, with the day temperatures ranging from 18° C. to 35° C. and night temperatures ranging from 16° C. to 25° C. Plants of 'DANCAT153' were fertilized up to a level of 59 ppm N, 35.4 ppm P and 94.4 ppm K.

Color references are made to The Royal Horticultural Society Colour Chart (R.H.S.), 2001 edition, except where general colors of ordinary significance are used. Color values were taken under daylight conditions at approximately noon in Moshav Mishmar Hashiva, Israel. The age of the 'DANCAT153' plants described is 12 weeks.

Parentage: *Torenia* 'DANCATBLUE' (patented, U.S. Plant Pat. No. 16,949.

Propagation: Tissue culture and soft tip cuttings.

Plant:

*Form.*—Bush, cascading.

*Growth habit.*—Compact, rounded.

*Height.*—About 15 cm.

*Spread.*—60 cm to 80 cm.

*Cold tolerance.*—Frost tender. Temperatures below 5° C. may damage plants.

*Vigor.*—Vigorous growth; plants are fully grown in 3 months from planting cutting in during summer season.

Stem:

*Color.*—Yellow-green, RHS 144B.

*Length.*—About 25 cm.

*Diameter.*—About 2 mm.

*Pubescence.*—Minimal.

*Branching.*—About 5 to 10 main branches grow from the base and split into hundreds of secondary and tertiary branches.

*Length of internodes.*—1.5 cm to 3.5 cm.

Foliage:

*Overall shape.*—Triangular-cordate.

*Apex.*—Acute.

*Base.*—Cordate.

*Size of leaf.*—Width: 1.5 cm to 3 cm. Length: About 3.5 cm.

*Margin.*—Serrate.

*Color* (*mature*).—Center color of leaf: Yellow-green, RHS 146A. Upper side: Yellow-green, RHS 146A. Under side: Yellow-green, RHS 146B.

*Color* (*immature*).—Center color of leaf: Yellow-green, RHS 144A. Upper side: Yellow-green, RHS 144A. Under side: Yellow-green, RHS 144B.

*Leaf texture.*—Smooth, few hairs on every leaf.

*Venation.*—Pattern: Anastomose. Color: Upper surface: Yellow-green, RHS 146A. Lower surface: Yellow-green, RHS 144B.

*Petioles.*—Length: About 0.4 cm to 1 cm. Diameter: About 2 mm. Color: Yellow-green, RHS 144B.

Flowers:

*Blooming period.*—All year round in a moderate climate or in a greenhouse environment. In Israel, flowering year round in moderate climate.

*Flowering response time.*—About 2–3 weeks from planting.

*Flowering stem.*—flowers appear along the growing stems.

*Quantity of flowers.*—Per stem: About 4 to 8; Per plant: About 100 to 200.

*Flowering longevity.*—On the plant: About 2 to 4 days, depending on temperature.

*Type.*—Single

*Shape.*—Overall: funnel form; 5-winged; Corolla tube: cylindrical or often broadened above; Corolla: 2-lipped, the upper lip faintly 2-lobed, the lower lip 3-lobed.

*Orientation at opening.*—Slanted upward.

*Fragrance.*—None.

*Flower size.*—Depth: About 3 cm. Width: About 3.5 cm.

*Bud.*—Shape: Oblong, cylindrical, ellipsoid, 5-winged.

*Size.*—Length: About 10 mm to 15 mm. Diameter: About 10 mm.

*Color.*—Apex: Yellow-green, RHS N144C. Base: Yellow-green, RHS 144A.

*Texture.*—Pubescence on winged edges.

*Floral tube.*—Length: About 2 cm. Width: About 0.5 cm to 1 cm. Color: Outside: Green-white, RHS 157A on lower side, greyed-yellow, RHS 162C middle, and white, RHS 155C upper side. Inside: White, RHS 155C at apex and white, RHS 155A at base and yellow, RHS 9A middle.

*Petals.*—Number: Four, fused. Length: Upper Petal: About 1.5 cm; Side Petals: About 2 cm; Lower Petal: About 1 cm. Width: Upper Petal: About 2.5 cm; Side Petals: About 1 cm; Lower Petal: About 1.5 cm. Shape: Upper Petal: Overall: spatulate, Apex: rounded, Base: fused; Side Petals: Overall: spatulate, Apex: rounded, Base: fused; Lower: Overall: spatulate, Apex: rounded, Base: fused. Margin: Undulated. Color: (RHS 2005 mini colour chart referenced for white petal color). Mature Petals: Flower is white with a yellow blotch. Upper Surface: Upper Petal: White, RHS N999D, and margin, white, RHS N999D; Side Petals: White, RHS N999D, and margin, white, RHS N999D; Lower Petal: Primarily white, RHS N999D, with yellow, RHS 9A blotch in the middle near base, and white, RHS N999D color surrounding blotch and near base, and margin white, RHS N999D. Lower Surface: Upper Petal: White, RHS N999D, and margin, white, RHS N999D; Side Petals: White, RHS N999D, and margin, white, RHS N999D; Lower Petal: Near apex, White, RHS N999D, and near base, white, RHS 155D, and margin, white, RHS N999D. Throat: Upper throat: White, RHS 155A; Lower throat: Yellow, RHS 8A. Immature Petals: Upper Surface: Upper Petal: White, RHS N999D, and margin white, RHS N999D; Side Petals: White, RHS N999D, and margin, white, RHS N999D; Lower Petal: Primarily white, RHS N999D, with yellow, RHS 4A blotch in the middle near base, and margin white, RHS N999D color surrounding blotch and near base. Lower Surface: Upper Petal: White, RHS N999D, and margin white, RHS N999D; Side Petals: White, RHS N999D, and margin white, RHS N999D; Lower Petal: White, RHS N999D, and margin white, RHS N999D; Throat: Center of Flower: White, RHS 155A.

*Number.*—5. Length: About 1.5 cm. Width: About 0.8 cm. Shape: Two-lobed, 5-winged. Apex: Acute. Base: Wedge shaped. Margin: Undulated. Color: Yellow-green, RHS 145A.

*Peduncle.*—Length: About 1 cm to 2 cm. Diameter: About 2 mm. Color: Yellow-green, RHS 144A.

Reproductive organs:

*Androecium.*—Stamen: Number: 2 pairs per flower, fused. Color: White, RHS 155D. Anther: Length: About 0.4 cm (upper anther shorter–about 0.3 cm); Width: About 0.1 cm. Color: Yellow-white, RHS 158A. Spur: Not Present. Filament: Length: About 1.5 cm; lower filaments are shorter about 0.5 cm. Width: About 0.1 cm. Color: White, RHS 155D. Pollen: Amount: Sparse. Color: White, RHS N155B. Requirements for pollination: Young flowers, vital pollen, and receptive, open stigma.

*Gynoecium.*—Pistil: Number: One per flower. Length: About 2 cm. Stigma: Length: About 0.2 cm. Width: About 0.3 cm. Color: White, RHS 155C. Style: Length: About 1.3 cm. Color: White, RHS 155C. Ovary: Number: 1. Length: About 0.5 cm. Width: About 0.2 cm. Color: Yellow-green, RHS 145A.

Seed/fruit: None.

Pest/disease resistance and/or susceptibility: A standard preventative spray program is sufficient as no susceptibility was observed.

Temperature tolerance: Sensitive to temperatures below 5° C.

I claim:

1. A new and distinct *Torenia* plant named 'DANCAT153', as illustrated and described herein.

* * * * *